(12) United States Patent
Bhaskaran et al.

(10) Patent No.: US 10,561,678 B2
(45) Date of Patent: Feb. 18, 2020

(54) COMPOSITION FOR TREATING NEUROPATHY, PROCESS AND METHOD OF TREATMENT THEREOF

(71) Applicant: Indus Biotech Private Limited, Pune, Maharashtra (IN)

(72) Inventors: Sunil Bhaskaran, Pune (IN); Mohan Vishwaraman, Pune (IN)

(73) Assignee: Indus Biotech Private Limited, Pune (IN)

(*) Notice: Subject to any disclaimer, the term of this patent is extended or adjusted under 35 U.S.C. 154(b) by 0 days.

(21) Appl. No.: 16/023,068

(22) Filed: Jun. 29, 2018

(65) Prior Publication Data

US 2018/0344755 A1    Dec. 6, 2018

Related U.S. Application Data

(62) Division of application No. 14/888,538, filed as application No. PCT/IB2014/060379 on Apr. 2, 2014, now Pat. No. 10,046,003.

(30) Foreign Application Priority Data

Apr. 2, 2013   (IN) .......................... 1286/MUM/2013

(51) Int. Cl.
*A61K 31/70* (2006.01)
*A61K 31/075* (2006.01)
*A61K 31/7028* (2006.01)
*A61K 36/48* (2006.01)

(52) U.S. Cl.
CPC ........ *A61K 31/7028* (2013.01); *A61K 31/075* (2013.01); *A61K 31/70* (2013.01); *A61K 36/48* (2013.01)

(58) Field of Classification Search
USPC .......................................................... 514/25
See application file for complete search history.

(56) References Cited

U.S. PATENT DOCUMENTS

| 3,107,605 A | 10/1963 | Aldrich |
| 6,451,355 B1 | 9/2002 | Reisner |
| 7,553,501 B2 | 6/2009 | Rangel |

FOREIGN PATENT DOCUMENTS

| WO | 2004/100968 A2 | 11/2004 |
| WO | 2005/084323 A2 | 9/2005 |

OTHER PUBLICATIONS

Morani et al, Asia Pacific Journal of Tropical Medicine, 2012, pp. 385-390.*
Bioscience Advanced Nutrition—products—Createch Maxcell. Aug. 8, 2009.
Varshney, I.P. et al, "Isolation of Ethyl Galactoside from Trigonella Corniculata seeds." Planta Medica. (1974) vol. 26, No. 1, pp. 26-32.
Preet, A. et al. "Restoration of ultrastructural and biochemical changes in alloxan-induced diabetic rat sciatic nerve on treatment with Na3VO4 and Trigonella—a promising antidiabetic agent." Molecular and Cellular Biochemistry (2005), vol. 278, No. 1 &2, pp. 21-31.
TKDL Abstract No. MA3/256 & Bayaaz-e-Kabir, vol. II (Compiled), Daftar-al-Maseeh, Karol Bagh, New Delhi, 1938 "Raughan-e-Shifa."
David H. Honig, et al., "Isolation of Ethyl α-D-Galactopyranoside and Pinitol from Hexane-Ethanol Extracted Soybean Flakes," Agricultural and Food Chemistry, vol. 19, No. 3, pp. 543-546.
Aashish S. Morani, et al., "Ameliorative effects of standardized extract from Trigonella foenum-graecum L. seeds on painful peripheral neuropathy in rats," Asian Pacific Journal of Tropical Medicine, (online May 20, 2012) pp. 385-390.
International Search Report and Written Opinion of the ISA for PCT/IB2014/060379, ISA/AU, Woden ACT, dated Jul. 7, 2014.
International Preliminary Report on Patentability for PCT/IB2014/060379/, IB, Geneva, dated Oct. 6, 2015.
Brekhman et al., Ann, Rev, Pharmacol., 1969, 9, 419-430.
Honig et al., Agr. & Food Chem. 1971, 19(3), 543-546.
Kim et al., Eur. J. Clinical Nutr., 2005, 59, 456-458.
Remington: The Science and Practice of Pharmacy, 21 Ed., 2005, 745-753.

* cited by examiner

*Primary Examiner* — Ganapathy Krishnan
(74) *Attorney, Agent, or Firm* — Harness, Dickey & Pierce, P.L.C.

(57) ABSTRACT

The present disclosure relates to a composition comprising eleutheroside-C, pinitol and sugars optionally along with pharmaceutically acceptable excipient or a combination thereof; a process of obtaining said composition from fenugreek seeds, a method of treating neuropathic pain or managing neuropathy, and the use of the said composition in treating neuropathic pain or managing neuropathy.

10 Claims, 5 Drawing Sheets

COMPOSITION FOR TREATING NEUROPATHY, PROCESS AND METHOD OF TREATMENT THEREOF

TECHNICAL FIELD

The present disclosure relates to a composition comprising eleutheroside-C, pinitol and sugars optionally along with pharmaceutically acceptable excipient or a combination thereof. The present disclosure also relates to a process of obtaining said composition from *Trigonella* species, a method of treating neuropathic pain or managing neuropathy, and the use of the said composition in treating neuropathic pain or managing neuropathy.

BACKGROUND OF THE DISCLOSURE

Neuropathic pain is a severe pathological condition of the nervous system. Neuropathic pain results from damage or abnormal function of the central or peripheral nervous system. Neuropathic pain is caused by lesion or inflammation of the nervous system and is relatively common with an incidence estimated at 0.6% to 1.5% in the Indian population. Neuropathic pain is probably multifactorial pathophysiological process.

Patients with neuropathic pain frequently report sensory abnormalities including burning sensations, as unpleasant abnormal sensation (dysesthesia), an increased response to painful stimuli (hyperalgesia), and pain in response to a stimulus that does not normally provoke pain (allodynia).

Hyperalgesia is increased pain sensitivity or a state of increased intensity of pain sensation induced by either noxious or ordinarily non-noxious stimulation of peripheral tissue. Allodynia is pain in response to a non-nociceptive stimulus. Hyperalgesia and allodynia are classified according to the type of stimulus which elicits the sensation of pain. Thermal (heat or cold) stimuli or mechanical brush, pinch, or pressure stimuli are most often used. In addition, moving (dynamic) or static mechanical touch stimuli are being used. Thereby, mechanical and thermal (heat or cold) hyperalgesia and mechanical dynamic allodynia can be differentiated.

Peripheral nerves carry information to and from the brain. They also carry signals to and from the spinal cord to the rest of the body. Peripheral neuropathy means these nerves don't work properly. Peripheral neuropathy may be due to damage to a single nerve or a nerve group. Because of this, pain sensitivity for anything that is too hot or cold may get lost. Patients with peripheral neuropathy may have tingling, numbness, unusual sensations, weakness, or burning pain in the affected area. The symptoms are symmetrical and involve both hands and feet.

Peripheral neuropathy is disorder of nerve(s) apart from the brain and spinal cord. Peripheral neuropathy can involve different nerve types, including motor, sensory, and autonomic nerves. Peripheral neuropathy can also be categorized by the size of the nerve fibers involved, large or small.

Mononeuropathy is a type of damage to nerves outside the brain and spinal cord (peripheral neuropathy). Mononeuropathy is most often caused by injury, although body-wide (systemic) disorders may cause isolated nerve damage. Long-term pressure on a nerve due to swelling or injury can result in Mononeuropathy. The covering of the nerve (myelin sheath) or part of the nerve cell (the axon) may be damaged. This damage slows or prevents signals from traveling through the damaged nerves. Mononeuropathy may involve any part of the body.

Some of the common forms of Mononeuropathy include:
Axillary nerve dysfunction (Axillary nerve palsy)
Carpal tunnel syndrome (median nerve dysfunction)
Femoral nerve dysfunction
Radial nerve dysfunction
Sciatic nerve dysfunction (sciatica)
Ulnar nerve dysfunction (cubital tunnel syndrome)
Existing Therapies for Neuropathic Pain:

Transcutaneous electrical nerve stimulation (TENS) may help to relieve symptoms. In this therapy, adhesive electrodes are placed on the skin and a gentle electric current is delivered through the electrodes at varying frequencies. TENS should be applied for 30 minutes daily for about a month. TENS is an inexpensive, noninvasive, self-administered technique that delivers pulsed electrical currents across the intact surface of the skin to relieve pain. The technique has some drawbacks such as use of TENS is likely to be less effective on areas of numb skin/decreased sensation due to nerve damage. It may also cause skin irritation due to the inability to feel currents until they are too high. There is an unknown level of risk when placing electrodes over an infection (possible spreading due to muscle contractions), but cross contamination with the electrodes themselves is of greater concern. TENS should also be used with caution in people with epilepsy or pregnant women.

Acupuncture involves the insertion of thin needles into various points on your body. Acupuncture may reduce symptoms in people with peripheral neuropathy. The therapy has some drawbacks that the patient may suffer from various infectious diseases, if the needles are re-used or not sterile. The effectiveness of acupuncture varies from person to person. Few complications have been reported due to the use of needles. If the needles are not inserted properly, it may lead to organ rupture or infection.

Although lot of medications and therapies are available to deal with neuropathic pain or neuropathy, they are with either side effects or are expensive over a long period of time. Hence there is a need to come up with such a novel composition that would not only deal with the pain but also would be cost effective.

Existing Medications:

Many types of medications have been reported to relieve the pain of peripheral neuropathy, including: Pain relievers, non-steroidal anti-inflammatory drugs, Medications containing opioids, such as tramadol (Ultram ER) or oxycodone (Roxicodone) etc. These drugs lead to dependence and addiction, so these drugs are generally prescribed only when other treatments fail. Capsaicin, A cream containing this naturally occurring substance found in hot peppers has shown modest improvements in peripheral neuropathy symptoms. Lidocaine patch may help reduce pain from peripheral neuropathy with side effects such as redness, swelling, irritation, itchiness.

Certain tricyclic antidepressant medications, such as amitriptyline, doxepin and nortriptyline (Aventyl, Pamelor), have been found to help relieve pain by interfering with chemical processes in brain and spinal cord that cause to feel pain. But they have shown many side effects such as dry mouth, nausea, drowsiness, dizziness, decreased appetite and constipation. Pregabalin can be used as an initial treatment for neuropathic pain. The two most common side effects of pregabalin are: dizziness, tiredness.

Alpha-lipoic acid is used as a treatment for peripheral neuropathy in Europe for years. This antioxidant may help reduce the symptoms of peripheral neuropathy. Side effects may include stomach upset, skin rash and it may affect blood sugar levels also.

Fenugreek (*Trigonella foenum-graecum*) is rich in phytochemicals and has traditionally been used as a food, forage and medicinal plant. Fenugreek has a long history of medical uses in Ayurvedic and Chinese medicine, and has been used for numerous indications, including labor induction, aiding digestion, and as a general tonic to improve metabolism and health.

Fenugreek is rich in chemical constituents. Fenugreek seed contains carbohydrates, mainly mucilaginous fiber (galactomannans); proteins high in lysine and tryptophan; fixed oils (lipids); pyridine-type alkaloids, mainly trigonelline, choline, gentianine, and carpaine; the flavonoids apigenin, luteolin, orientin, quercetin, vitexin, and isovitexin; free amino acids, such as 4-hydroxyisoleucine, arginine, histidine, and lysine; calcium and iron; saponins, glycosides yielding steroidal sapogenins on hydrolysis (diosgenin, yamogenin, tigogenin, neotigogenin); cholesterol and sitosterol; vitamins A, B1, C, and nicotinic acid; volatile oils (n-alkanes and sesquiterpenes) and sugars such as raffinose, stachyose, sucrose, fructose, mannose, verbascose and xylose.

The seeds also contain the saponin fenugrin B, coumarin compounds. The seed is also responsible for fixed oil. Several C-glycoside flavones have been identified in the seeds of fenugreek. These include vitexin, vitexin glycoside, and an arabinoside of orientin (iso-orientin), minor steroidal sapogenins (fenugreekine, smilagenin, sarsasapogenin, yuccagenin), and up to 50% of mucilaginous fiber.

These different chemical constituents have shown diverse therapeutic effects. The component called fenugreekine; a steroidal sapogenin peptide ester has hypoglycemic properties and has shown improved pancreatic function. It helps to delay gastric emptying, slow carbohydrate absorption, and inhibit glucose transport in humans. Trigonelline is suggested to exert hypoglycemic effects in healthy patients without diabetes. The steroidal saponins (diosgenin, yamogenin, tigogenin and neotigogenin) are thought to inhibit cholesterol absorption and synthesis and hence its potential role in arteriosclerosis. It is also used topically to treat inflammation, and to promote postpartum lactation in animals. At present diosgenin, a steroid sapogenin is used in the manufacture of birth control pills. Plant phenolics have potential health benefits mainly due to their antioxidant properties such as reactive oxygen species (ROS) scavenging and inhibition, electrophile scavenging and metal chelation. They have also been reported to exhibit pharmacological properties such as antitumor, antiviral, antimicrobial, anti-inflammatory, hypotensive and antioxidant activity.

Eleutherococcus senticosus which is formerly labeled as Siberian *Ginseng*, is often referred to also as *Ciwujia E.*, thorny *ginseng* or Eleuthero. This botanical source is a thorny bush indigenous to the Taiga region of the Far East, which includes southeastern Russia, northern China, Japan and Korea. The key active ingredient of Eleuthero is Eleutherosides A-G. This group is chemically heterogenous. Eleutheroside A is the ubiquitous phytosterol daucosterol. Eleutheroside B (syringin) is a phenyl propanoid, whereas Eleutheroside B1 is a coumarine derivative. Eleutheroside C is ethyl-α-D-galactoside. Eleutheroside D and its diastereoisomer Eleutheroside E are lignin derivatives. Eleuthero is the only reported plant source for Eleutherosides. The structures are as follows:

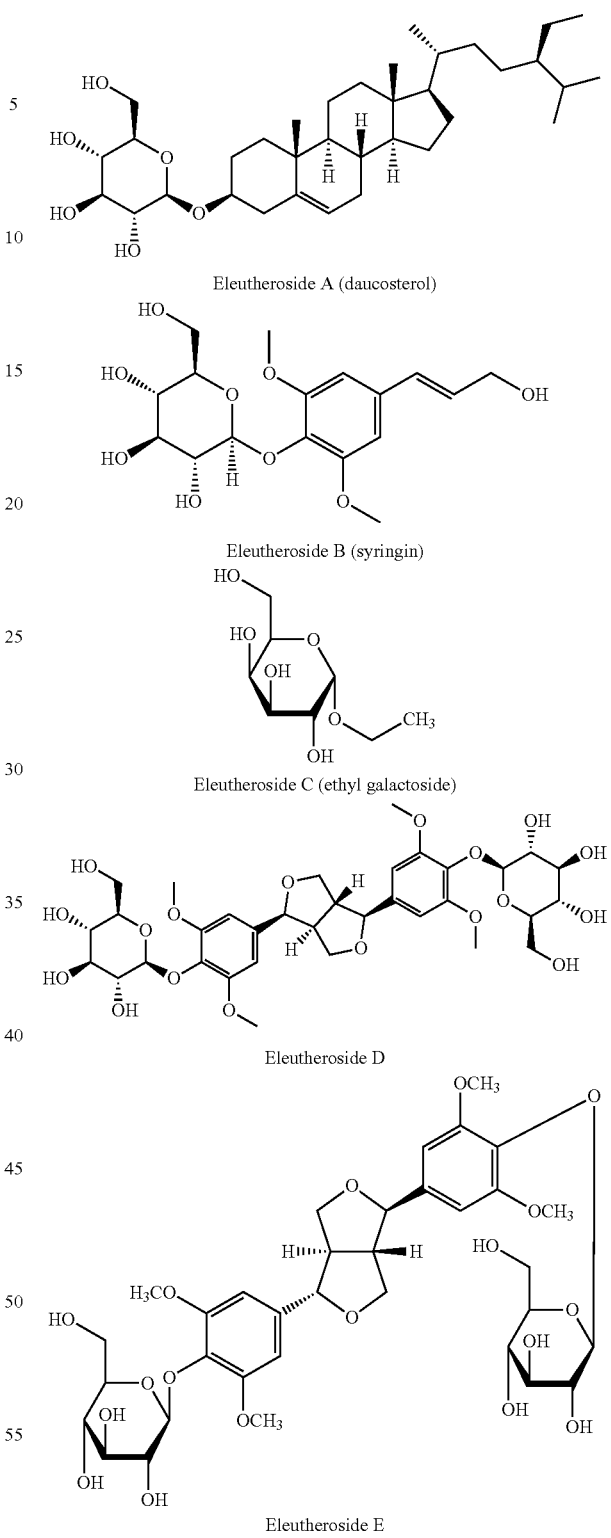

Eleutheroside A (daucosterol)

Eleutheroside B (syringin)

Eleutheroside C (ethyl galactoside)

Eleutheroside D

Eleutheroside E

Eleutherosides fractionation from fenugreek is not reported in the prior art.

One of the nine stereoisomers of Inositol is Myo-inositol. This myo-inositol act as a precursor for the synthesis of pinitol that is most abundant in soybeans.

Pinitol is a methylated cyclic sugar alcohol (cyclitol). Pinitol is a cyclitol corresponding to the methylated form of D-chiro-inositol and more concretely it is 3-O-methyl-1,2,4 cis-3,5,6 transhexahydroxycyclohexanol. It has been found in bacteria, fungi, algae and plants. It also occurs widely in plants such as: soya, in leaves of *Bougainvillea spectabilis*, etc.

Pinitol can also be obtained by chemical synthesis, but until now the process has been very expensive. It is a normal component of the human diet. It is present in soya at about 1% of dry weight. It plays an important role in osmoregulation and osmoprotection. Pinitol fractionation from fenugreek is not reported in the prior art.

There are no teachings in the prior art which disclose that Eleutherosides and pinitol are present in and obtained from fenugreek.

The present disclosure provides a composition and a process of obtaining the composition which aims at addressing the challenges existing in the field of treating neuropathy related disorders.

BRIEF DESCRIPTION OF THE ACCOMPANYING FIGURES

The features of the present disclosure will become more fully apparent from the following description taken in conjunction with the accompanying figures. The figures depict only several embodiments in accordance with the disclosure and are therefore, not to be considered limiting of its scope. The disclosure will be described with additional specificity and detail through use of the accompanying figures.

STATEMENT OF THE DISCLOSURE

Figure 1:
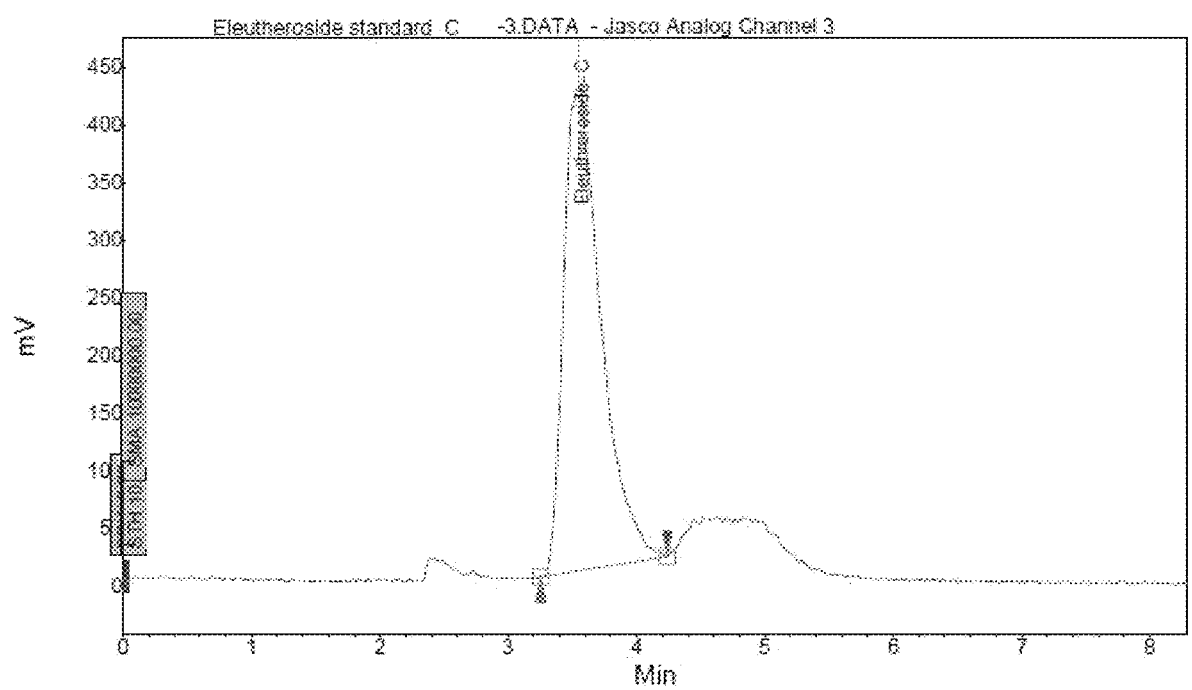
FIG. 1 illustrates the HPLC standard of the compound Eleutheroside-C

Accordingly, the present disclosure relates to a composition comprising eleutheroside-C, pinitol and sugars optionally along with pharmaceutically acceptable excipient or a combination thereof; a process of obtaining a composition of the present disclosure, said process comprising acts of (a) contacting sample of *Trigonella* species with a solvent in a chromatographic column, followed by draining the solvent to obtain de-lipidized solution, (b) extracting the de-lipidized solution with hydro-alcohol mixture to obtain a first extract, (c) exposing the first extract to ion exchange column, followed by passing the extract through an adsorbent column to obtain a second extract, (d) heating the second extract and re-exposing the same to ion exchange column followed by optionally filtering and neutralizing the extract and (e) concentrating the extract of step (d) to obtain the composition of the present disclosure; a method of treating neuropathic pain or managing neuropathy, said method comprising administering to a subject in need thereof, a therapeutically effective amount of a composition comprising eleutheroside-C, pinitol and sugars, optionally along with pharmaceutically acceptable excipient or a combination thereof and a composition comprising eleutheroside-C, pinitol and sugars, optionally along with pharmaceutically acceptable excipient for use in treating neuropathic pain or managing neuropathy.

DETAILED DESCRIPTION OF THE DISCLOSURE

The present disclosure relates to a composition comprising eleutheroside-C, pinitol and sugars optionally along with pharmaceutically acceptable excipient or a combination thereof.

In an embodiment of the present disclosure, the eleutheroside-C and pinitol are each at a concentration ranging from about 1% to about 50%.

In another embodiment of the present disclosure, the sugars are selected from a group comprising raffinose, stachyose, glucose, fructose, sucrose, xylose and galactose or any combination thereof; wherein the sugars are preferably sucrose, raffinose and stachyose; and wherein the sugars are at a concentration ranging from about 1% to about 70%.

In yet another embodiment of the present disclosure, the composition is obtained from *Trigonella* species, preferably *Trigonella foenum graecum*.

In still another embodiment of the present disclosure, the pharmaceutically acceptable excipient is selected from a group comprising granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, plant derived sugars, preservatives, suspending agents, emulsifying agents, plant cellulosic material and spheronization agents or any combination thereof.

In still another embodiment of the present disclosure, the composition is formulated into various dosage forms selected from a group comprising oral formulations like tablet, troches, lozenges, aqueous or oily suspensions, ointment, patch, gel, lotion, capsule, emulsion, creams, spray, drops, dispersible powders or granules, emulsion in hard or soft gel capsules, inhalers, nebulizers, intravenous injection, intravenous solutions, intramuscular injections, intramuscular depot, subcutaneous injection, percutaneous injection, medical food, phytoceuticals, nutraceuticals and food stuffs or any combination thereof.

The present disclosure also relates to a process of obtaining a composition of the present disclosure, said process comprising acts of:
a) contacting sample of *Trigonella* species with a solvent in a chromatographic column, followed by draining the solvent to obtain de-lipidized solution;
b) extracting the de-lipidized solution with hydro-alcohol mixture to obtain a first extract;
c) exposing the first extract to ion exchange column, followed by passing the extract through an adsorbent column to obtain a second extract;
d) heating the second extract and re-exposing the same to ion exchange column followed by optionally filtering and neutralizing the extract; and
e) concentrating the extract of step (d) to obtain the composition of the present disclosure.

In an embodiment of the present disclosure, the sample of step (a) is a seed of *Trigonella* species, preferably seed of *Trigonella foenum graecum*; and wherein the seed is flaked.

The method as claimed in claim 7, wherein the solvent is N-butyl alcohol; and wherein the solvent exposure is for a time period ranging from about 4 hr to about 8 hr, preferably for about 6 hr.

In another embodiment of the present disclosure, the hydro alcohol mixture comprises water:ethyl alcohol at a ratio ranging from about 1:0.5 to about 1:3; and wherein the extraction is carried out for a time period ranging from about 6 hr to about 10 hr, preferably for about 8 hr and at a temperature ranging from about 40° C. to about 80° C., preferably for about 62° C. to about 65° C.

In yet another embodiment of the present disclosure, the exposure of the first extract to the ion exchange column is for a time period ranging from about 4 hr to about 6 hr, preferably for about 5 hr; and wherein the ion exchange column is a cation exchange column.

In still another embodiment of the present disclosure, the adsorbent column comprises a macro reticular polymeric adsorbent.

In still another embodiment of the present disclosure, the heating is carried out at a temperature ranging from about 50° C. to about 70° C., preferably at about 60° C. to about 65° C.; wherein the ion exchange column comprises a cation exchange resin; and wherein the neutralization is carried out by exposure to neutralizing macro porous type 1 resin.

In still another embodiment of the present disclosure, the concentration is under vacuum carried out at a temperature ranging from about 40° C. to about 50° C., preferably at about 45° C.

The present disclosure also relates to a method of treating neuropathic pain or managing neuropathy, said method comprising administering to a subject in need thereof, a therapeutically effective amount of a composition comprising eleutheroside-C, pinitol and sugars, optionally along with pharmaceutically acceptable excipient or a combination thereof.

In an embodiment of the present disclosure, the neuropathy is selected from a group of indications comprising Sciatica, Nerve compression syndrome, Carpal tunnel syndrome, Axillary nerve palsy, Neuropraxia, Neurotmesis and Axonotmesis or any combination thereof.

In another embodiment of the present disclosure, the neuropathy can be caused by trauma, alcoholism, viral infections, autoimmune disorders, bacterial infections or chemotherapy treatments.

In yet another embodiment of the present disclosure, the composition is administered at a dose ranging from about 1 mg/kg to about 100 mg/kg, preferably ranging from about 1 mg/kg to about 25 mg/kg, more preferably ranging from about 3 mg/kg to about 30 mg/kg of body weight of the subject per day; and wherein the subject is a mammal, including human being.

The present disclosure also relates to a composition comprising eleutheroside-C, pinitol and sugars, optionally along with pharmaceutically acceptable excipient for use in treating neuropathic pain or managing neuropathy.

The present disclosure relates to composition comprising Eleutheroside C and Pinitol along with other sugars from Fenugreek originating from different geographical locations.

The present disclosure also relates to a unique process which is able to isolate enriched forms of Eleutheroside C and Pinitol along with other sugars from fenugreek removing all other active principles such as amino acids, alkaloids, saponins etc. It is important to note that presence and isolation of Eleutheroside C from fenugreek is not yet reported in the literature.

In an embodiment of the present disclosure, the above composition from fenugreek comprising Eleutheroside, pinitol and other sugars demonstrated significant efficacy in neuropathy.

In an embodiment of the present disclosure, the use of Eleutheroside C along with Pinitol and sugars in a composition for treating neuropathy was not known previously. Prior art has focused on isolating pinitol from soybean and for treating conditions associated with insulin resistance. But the isolation of pinitol along with other constituents has not been reported as yet.

The present disclosure relates to a composition for treatment of neuropathy in a subject in need thereof, said composition obtained from Fenugreek, comprising Eleutheroside-C, Pinitol along with fenugreek derived sugars and pharmaceutically acceptable excipients.

In an embodiment of the present disclosure, the fenugreek derived sugars are selected from a group comprising Raffinose, Stachyose, Glucose, Fructose, Sucrose, Xylose and Galactose or any combination thereof. In an embodiment of the present disclosure, the composition comprises Eleutheroside-C and Pinitol each at a concentration ranging from about 1-50% and fenugreek derived sugars at a concentration ranging from 1%-70%, optionally along with pharmaceutically acceptable excipients.

In another embodiment, the disclosure relates to a composition for the treatment of neuropathy in a subject in need thereof, wherein said neuropathy is selected from a group of indications comprising Sciatica, Nerve compression syndrome, Carpal tunnel syndrome, Axillary nerve palsy, Neuropraxia, Neurotmesis and Axonotmesis or any combination thereof.

In yet another embodiment of the present disclosure, pinitol is in the concentration ranging from about 1% to about 50%.

In still another embodiment of the present disclosure, Eleutheroside-C is in the concentration ranging from about 1% to about 50%.

In still another embodiment of the present disclosure, fenugreek derived sugars are in the concentration ranging from about 1% to about 70%.

In still another embodiment of the present disclosure, the fenugreek derived sugars such as Raffinose, Stachyose, Glucose, Fructose, Sucrose, Xylose and Galactose are in the concentration ranging from about 1% to about 70%.

In still another embodiment of the present disclosure, administration of an oral pharmaceutical composition obtained from Fenugreek, comprising Eleutheroside-C, Pinitol and fenugreek derived sugars optionally along with pharmaceutically acceptable excipients.

In still another embodiment of the present disclosure, oral formulations like tablets, capsules, liquid orals, and powders or granules are prepared by using excipients.

In still another embodiment of the present disclosure, excipients are selected from a group comprising granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, plant derived sugars, preservatives, suspending agents, emulsifying agents, plant cellulosic material and spheronization agents or any combination thereof.

In still another embodiment of the present disclosure, the composition is obtained from *Trigonella* species, preferably *Trigonella foenum graecum*.

In still another embodiment of the present disclosure, the pinitol is obtained from plant source. The pinitol is obtained from *Trigonella foenum graecum*.

In still another embodiment of the present disclosure, the Eleutheroside-C is obtained from plant source. The Eleutheroside-C is obtained from *Trigonella foenum graecum*.

In still another embodiment of the present disclosure, sugars are obtained from plant source. The sugars are obtained from *Trigonella foenum graecum*.

In still another embodiment of the present disclosure, the composition is free of adverse effects.

The present disclosure further relates to a process for preparation of composition obtained from Fenugreek, comprising Eleutheroside-C, Pinitol and fenugreek derived sugars optionally along with pharmaceutically acceptable excipients, said process consisting acts of:

a. Flaking seeds of *Trigonella*
b. Extraction with hydro alcohol
c. Concentration
d. Re-extraction
e. Dilution
f. filtration
g. Column Purification
h. Reflux purification
i. Concentration
j. Evaporation
k. Drying
l. Grading
m. Granulation
n. Blending In an embodiment of the present disclosure, the term "test composition" involves a final product obtained from a process (as described in Examples 1, 2 and 3) explained below. It includes Eleutheroside-C, Pinitol and sugars optionally along with pharmaceutically acceptable excipients.

In still another embodiment of present disclosure, the composition is used in the treatment or management of neuropathy.

In an embodiment of the present disclosure, the term managing or management includes preventing and treating of a disease condition or disorder or ill effects or side effects. The term also encompasses maintenance of the optimum state and prevention of the further progress in the disease condition or disorder or ill effects or side effects.

Animal Models:

The partial sciatic nerve injury model (Seltzer et al., 1990) and sciatic nerve crush injury model (Zochodne and Ho, 1990) are the models of neuropathic pain induced by denervation of a peripheral nerve. Both the models induce the same level of thermal hyperalgesia and this thermal hyperalgesia was thought to be maintained by the spinal facilitatory state.

Source and Geographical Origin:

The source of the biological material employed in the present disclosure is fenugreek (*Trigonella foenum graecum*).

The geographical origin of the said biological material as utilized in the present disclosure is from the state of Madhya Pradesh and from the state of Rajasthan, in India.

EXAMPLES

A more complete understanding can be obtained by reference to the following specific examples, which are provided for purposes of illustration only and are not intended to limit the scope of the disclosure.

Example 1

Process for the Preparation of Composition 1:

450 g of Fenugreek seeds are flaked and packed in a column. N-Butyl alcohol is passed through the layer of Fenugreek by circulation for 6 hours and the Fenugreek layer is drained free of Butyl alcohol. The de-lipidized Fenugreek from the previous step is subjected to extraction using hydro-alcohol mixture comprising of water:ethyl alcohol (40:60) at a temperature of about 65° C. for 8 hours in counter current manner. The clear extract measuring 1500 ml in hot condition temperature between 65° C. is passed through a strong acid cation exchange resin column (glass column) in gel form over a period of 6 hours to remove amino acids. The resin bed is drained and the extract is cooled to room temperature. This extract is passed through a macro reticular polymeric adsorbent XAD1180 to trap large organic molecules such as saponins. The column remainder (the extract which comes out of the column) is heated to 58° C. and treated with Tulsion-T42 for a period of 2 hours to remove all remaining basic components such as residual alkaloids. After 2 hours the resin is filtered out to get a clear extract.

This extract is again passed through a neutralizing macro porous type 1 resin INDION830 which acts as a decolorization resin to remove colours. The resultant solution is concentrated under vacuum between temperatures 50° C. to evaporate remaining alcohols and moisture content to get a free flowing powder of 7 g of the Test Composition 1 in a dry form.

Example 1(a)

The Test composition of example 1 is analyzed using HPLC having ELSD detector, under the following conditions:

Equipment: JASCO-LC 2000 with ELSD 3300 (ALLTECH) Nitrogen flow: 1.3 lit/min
Temperature: 45° C.
Column: 150 mm×4.6 mm, Altima Amino 5µ (Grace)
Mobile Phase: Water:Acetonitrile gradient starting from 80% Acetonitrile to 65% over 20 minutes.
Mobile phase flow rate: 0.9 ml/min

| Compound | RT (min) |
| --- | --- |
| Eleutheroside-C | 3.6 |
| Pinitol | 4.7 |
| Sucrose | 7.6 |
| Raffinose | 11.2 |
| Stachyose | 16.2 |

Standardization is carried out using the following standards:

Eleutheroside-C: Reference Standard: Chemfaces catalog no. CFN99650. The HPLC standard for the compound eleutheroside-C is illustrated in FIG. 1.

Figure 2:
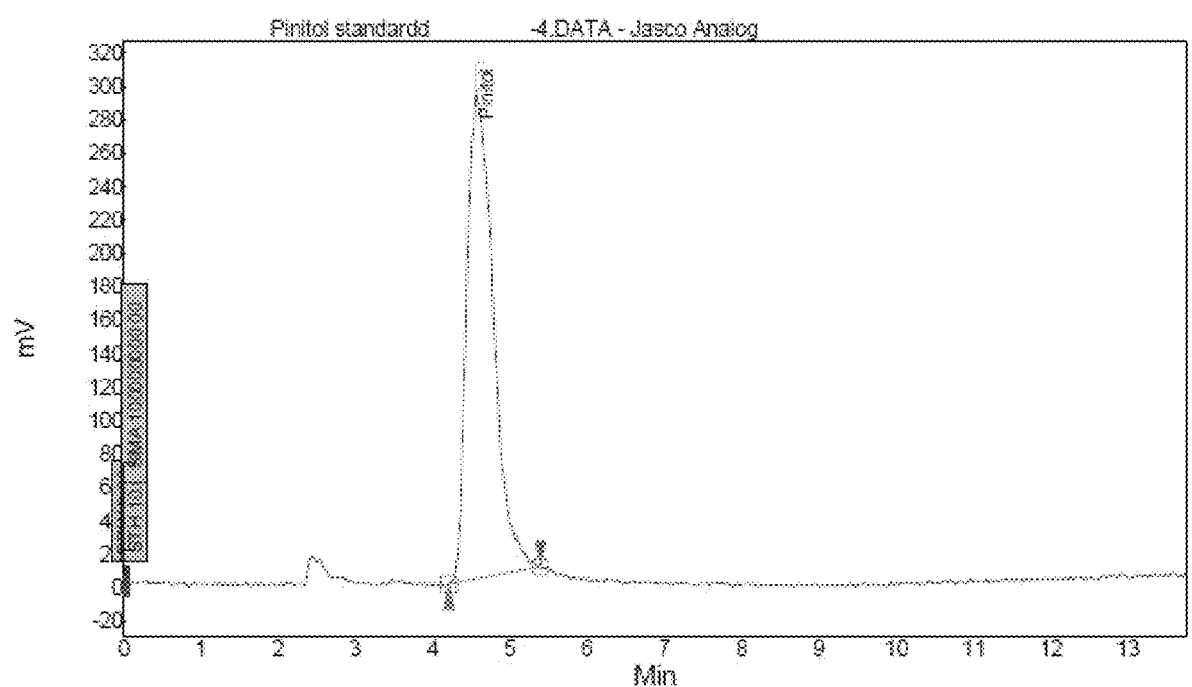
FIG. 2 illustrates the HPLC standard of the compound Pinitol

Pinitol: Reference Standard: Aldrich-Sigma catalog no. 441252. The HPLC standard for the compound pinitol is illustrated in FIG. 2.

| Compound | Test Composition 1 (from Example 1) |
| --- | --- |
| Eleutheroside-C | 30% |
| Pinitol | 48% |
| Sucrose | 6% |
| Raffinose | 6.5% |
| Stachyose | 9.5% |

Figure 3:
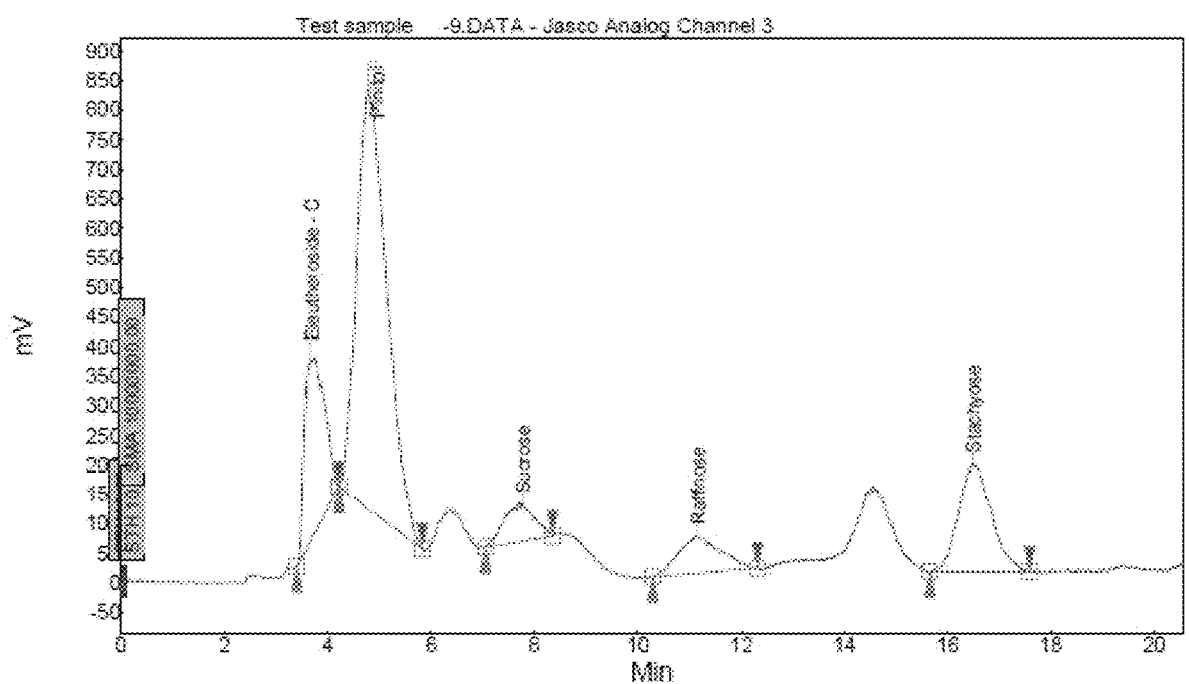
FIG. 3 illustrates the HPLC data for the test composition 1

The HPLC data for the test composition 1 (of example 1) is illustrated by FIG. 3.

Example 2

Process for the Preparation of Composition 2:

450 g of Fenugreek seeds are flaked and packed in a column. N-Butyl alcohol is passed through the layer of Fenugreek by circulation for 6 hours and the Fenugreek layer is drained free of Butyl alcohol. The de-lipidized Fenugreek from the previous step is subjected to extraction using hydro-alcohol mixture comprising of water:ethyl alcohol (30:70) at a temperature at about 62° C. for 8 hours in countercurrent manner. The clear extract measuring 1300 ml in hot condition temperature between 60° C. is passed through a strong acid cation exchange resin column (glass column) in gel form over a period of 5 hours to remove amino acids. The resin bed is drained and the extract was cooled to room temperature.

This extract is passed through a macro reticular polymeric adsorbent XAD1180 to trap large organic molecules such as saponins. The column remainder (the extract which comes out of the column) is heated to 60° C. and treated with Tulsion-T42 for a period of 2 hours to remove remaining basic components such as residual alkaloids. After 2 hours the resin is filtered out to get a clear extract. This extract was again passed through a neutralizing macro porous type 1 resin INDION830 to remove colors which acts as a decolorization resin. The resultant solution is concentrated under vacuum between temperatures 45° C. to evaporate remaining alcohols and moisture content to get a free flowing powder of 6.5 g of the Test Composition 2 in a dry form.

Example 3

Process for the Preparation of Composition 3:

450 g of Fenugreek seeds are flaked and packed in a column. N-Butyl alcohol is passed through the layer of Fenugreek by circulation for 6 hours and the Fenugreek layer was drained free of Butyl alcohol. The de-lipidized Fenugreek from the previous step is subjected to extraction using hydro-alcohol mixture comprising of water:ethyl alcohol (50:50) at a temperature at about 64° C. for 8 hours in countercurrent manner. The clear extract measuring 1250 ml in hot condition temperature between 65° C. is passed through a strong acid cation exchange resin column (glass column) in gel form over a period of 5 hours to remove amino acids. The resin bed is drained and the extract is cooled to room temperature. This extract is passed through a macro reticular polymeric adsorbent XAD1180 to trap large organic molecules such as saponins. The column remainder (the extract which comes out of the column) is heated to 60° C. and treated with Tulsion-T42 for a period of 2 hours to remove remaining basic components such as residual alkaloids. After 2 hours the resin is filtered out to get a clear extract. This extract is again passed through a neutralizing macro porous type 1 resin INDION830 to remove colors. The resultant solution is concentrated under vacuum between temperatures 45° C. to evaporate remaining alcohols and moisture content to get a free flowing powder of 6.5 g of the Test Composition 3 in a dry form.

Example 3(a)

The Test composition 3 is analyzed using HPLC having ELSD detector, under the following conditions as mentioned in example1(a).

Mobile Phase—Water:Acetonitrile gradient starting from 80% Acetonitrile to 65% over 20 minutes.
  Equipment: JASCO-LC 2000 with ELSD 3300 (ALLTECH)
  Nitrogen flow: 1.3 lit/min
  Temperature: 45° C.
  Column: 150 mm×4.6 mm, Altima Amino 5μ (Grace)
  Mobile Phase: Water:Acetonitrile gradient starting from 80% Acetonitrile to 65% over 20 minutes.
  Mobile phase flow rate: 0.9 ml/min

| Compound | RT (min) |
| --- | --- |
| Eleutheroside-C | 3.6 |
| Pinitol | 4.7 |
| Sucrose | 7.6 |
| Raffinose | 11.2 |
| Stachyose | 16.2 |

Standardization is carried out using the following standards:

Eleutheroside-C: Reference Standard: Chemfaces catalog no. CFN99650. The HPLC standard for the compound eleutheroside-C is illustrated in FIG. 1.

Pinitol: Reference Standard: Aldrich-Sigma catalog no. 441252. The HPLC standard for the compound pinitol is illustrated in FIG. 2.

| Compound | Test Composition (from Example 3) |
| --- | --- |
| Eleutheroside-C | 34% |
| Pinitol | 28% |
| Sucrose | 10% |
| Raffinose | 13% |
| Stachyose | 15% |

Figure 4:
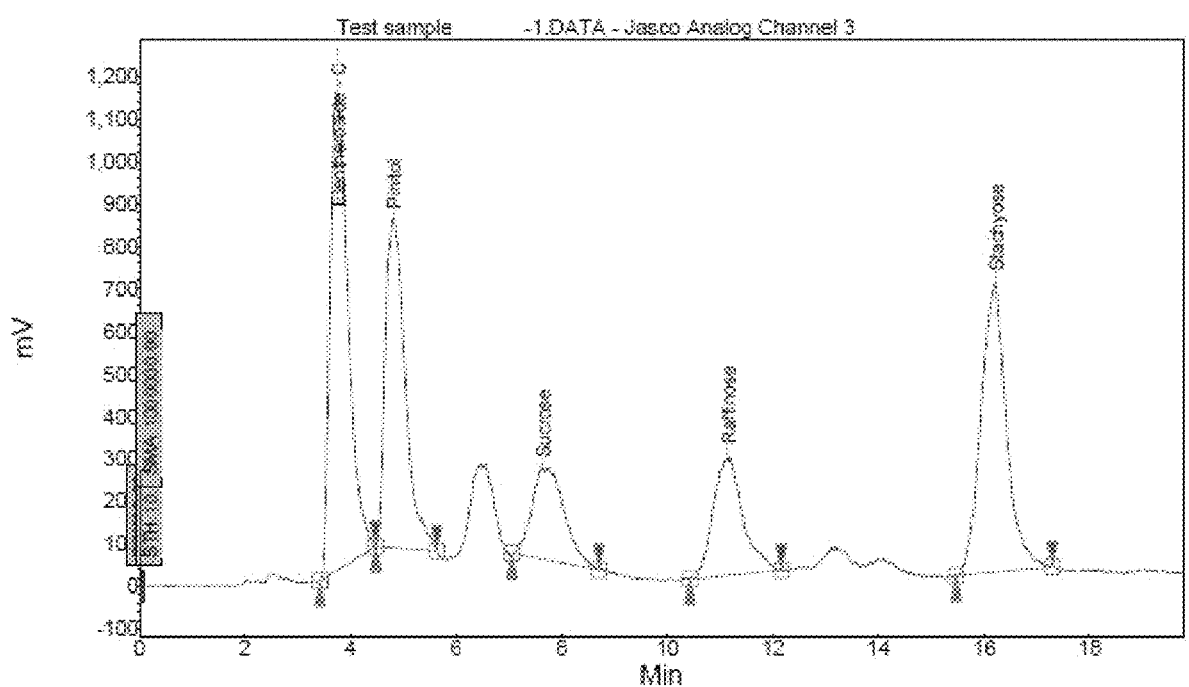
FIG. 4 illustrates the HPLC data for the test composition 3

The HPLC data for the test composition 3 (of example 3) is illustrated by FIG. 4.

The test composition 3 is further used in pre-clinical study for analyzing the efficacy of test composition in animal models and in patient study for neuropathy.

Example 4

Evaluation of Test Composition for Neuropathy

The partial sciatic nerve ligation (PSNL) or crush lesion to nerve fibres results in thermal hyperalgesia, thermal allodynia, mechanical hyperalgesia and mechanical allodynia which develop quickly (i.e. within hours post-injury) in the affected hind limb.

Three factors are thought to cause hyperalgesia in the sciatic nerve ligation model, first is the ectopic discharge generated from injured axons, the second is release of cytokines from the inflammatory cells around the injured nerve and the third is plastic changes in the sensory pathways to the spinal cord and brain. Injury to the mixed sciatic nerve damages motor as well as sensory fibres. Thus, the injuries have resulted in a central (spinal) sensitization of neurons leading to a reduction in thermal withdrawal latency.

Evaluation of Test Composition for its Effects Against Neuropathy

To study the Test Composition some of most commonly used models for neuropathic pain have been used which are:
  a. Partial Sciatic Nerve Ligation (PSNL)
  b. Sciatic Nerve Crush Injury (SCNI)

The parameters taken into consideration for these two studies:
  1. Mechanical Hyperalgesia
    a. Randall-Selitto paw pressure test
    b. Von Frey hair test
  2. Thermal Hyperalgesia
    a. Plantar test
  3. Cold Hyperalgesia
    a. Cold bath test
  4. Motor Nerve Conduction Velocity

TABLE 1

Methods to assess hyperalgesia or allodynia

| Sr. No. | Modality | Test Name (Most Common) | Test Method | Testing Site | Outcome Parameter |
|---|---|---|---|---|---|
| 1 | Mechanical | von Frey | Application of non-noxious calibrated static hairs on skin | Hindpaw, face | Force threshold to elicit paw withdrawal (static mechanical hyperalgesia*) |
| | | Randal Sellito | Application of linearly increasing mechanical force in noxious range on skin | Hindpaw | Force threshold to elicit paw withdrawal from noxious stimulus (mechanical hyperalgesia*) |
| 2 | Thermal | Plantar Hargreave's | Application of radiant heat on skin | Hindpaw | Time latency to elicit paw withdrawal (heat hyperalgesia) |
| 3 | Cold | Cold Bath | Animal placed in shallow cold water bath | Hindpaw | Time latency to elicit nociceptive or escape behaviors, duration and intensity of nociceptive behaviors (cold hyperalgasia) |
| 4. | Nerve conduction velocity | Motor Nerve conduction velocity | stimulating the sciatic and tibial nerves at sciatic and tibial notch | paws of rats | measuring the resultant onset latency and distance |

Grouping of Animals is Done in Following Manner:

Group I: Normal Group

The rats did not receive either surgery or injury for sciatic nerve. They received only vehicle (Distilled water).

Group II: Sham Group

The sciatic nerve of the rats is exposed, but they did not receive injury. They received only vehicle (Distilled water).

Group III: PSNL Control Group

The sciatic nerve of the rats is exposed and they received injury by a process where a 4-0 silk suture are inserted into the nerve with ⅜ curve, with a reverse-cutting mini needle and is tightly ligated so that the dorsal ⅓-½ of the nerve thickness are trapped in the ligature. They received only vehicle (Distilled water).

Group IV: Test Composition Treated Group (3 mg/kg)

The sciatic nerve of the rats is exposed and they received injury. They are treated with Test composition at a low dose of 3 mg/kg, p.o.

Group V: Test Composition Treated Group (10 mg/kg)

The sciatic nerve of the rats is exposed and they received injury. They are treated with Test composition at a medium dose of 10 mg/kg, p.o.

Group VI: Test Composition Treated Group (30 mg/kg)

The sciatic nerve of the rats is exposed and they received injury. They are treated with Test composition at a high dose of 30 mg/kg, p.o as shown in TABLE 2 below:

TABLE 2

| Group No. | Treatment | Dose (units) | Route of Administration | No. of animals (n) |
|---|---|---|---|---|
| 1 | Normal | Vehicle | Oral | 6 |
| 2 | Sham | Vehicle | Oral | 6 |
| 3 | PSNL Control | Vehicle | Oral | 6 |
| 4 | PSNL + Test Composition | 3 mg/kg | Oral | 6 |
| 5 | PSNL + Test Composition | 10 mg/kg | Oral | 6 |
| 6 | PSNL + Test Composition | 30 mg/kg | Oral | 6 |

Example 5

Effect of Test Composition on Partial Sciatic Nerve Ligation (PSNL) Induced Neuropathy in Rats Male wistar rats weighing 200-220 g average are used for the study. All the required parameters (pre-operative) are carried out in all rats before surgery. Under Ketamine anaesthesia (80 mg/kg) and aseptic conditions the right sciatic nerve is exposed at thigh level and a partial sciatic nerve injury is created by a standard protocol. The animals are allowed to recover after surgery for 2 days. Before initiation of treatment baseline reading is taken on day 0 and the doses are administered as described in above table 2 for 28 days. Data analysis is performed using Graph Pad Prism 5.0 software (Graph Pad San Diego, Calif.).

Statistical comparisons are made between drug treated groups and PSNL control animals. Data of disease activity index are statistically analyzed using two-way repeated ANOVA, Bonferroni's multiple range test is applied for post hoc analysis, while nerve conduction velocity is analyzed using one-way ANOVA, Dunnett's multiple range test is applied for post hoc analysis. A value of $p<0.05$ is considered to be statistically significant.

Example 6

Mechanical Hyperalgesia
A. Effect of TEST COMPOSITION on Mean Applied Force (g) in Randall-Selitto Paw Pressure Test:

Before initiation of treatment, baseline reading is taken on day 0 and the doses are administered for 28 days. As shown below table 3, on day 0, mean applied force in PSNL control rats is decreased significantly as compared to sham and normal group. This showed that Partial Sciatic nerve ligation resulted in significant development of mechanical hyperalgasia. Thus pain sensitivity is increased significantly due to mechanical hyperalgesia. However on day 28 of administration of Test composition, mechanical nociceptive threshold i.e. mean applied force significantly increased at higher doses (i.e. 10 mg/kg, 30 mg/kg) as compared to PSNL control rats. This shows that treatment with instant composition showed reduction in pain sensitivity. Thus instant composition shows efficacy in reducing neuropathic pain or managing neuropathy.

TABLE 3

Effect of TEST COMPOSITION on mean applied force (g) in Randall-Selitto paw tests in PSNL rats

| Days | Normal | Sham | PSNL Control | TEST COMPOSITION | | |
| --- | --- | --- | --- | --- | --- | --- |
| | | | | PSNL + 3 mg/kg | PSNL + 10 mg/kg | PSNL + 30 mg/kg |
| (Day 0) (Before Treatment) | 240.00 ± 20.12 | 235.00 ± 10.72 | 70.00 ± 5.00$^{\#\#\#}$ | 77.50 ± 13.08$^{ns}$ | 77.50 ± 9.01$^{ns}$ | 75.00 ± 12.24$^{ns}$ |
| 28 (After Treatment) | 262.50 ± 16.77 | 250.00 ± 10.72 | 77.50 ± 9.81$^{\#\#\#}$ | 132.50 ± 20.27 | 172.50 ± 13.28*** | 215.00 ± 10.00*** |

Data was analysed by Two-Way ANOVA followed by Bonferroni's post tests *p<0.05, p<0.01, *p<0.001 as compared with PSNL control group and $^{\#}$p<0.05, $^{\#\#}$p<0.01, $^{\#\#\#}$p<0.001 as compared with sham group on respective days, ns—non significant Example 7

Mechanical Hyperalgesia
B. Effect of Test Composition on Paw Withdrawal Threshold (g) in Von Frey Hair Test in PSNL Rats Before initiation of treatment baseline reading is taken on day 0 and the doses are administered for 28 days. As shown in below table 4, on day 0, mean paw-withdrawal threshold in PSNL control rats is decreased significantly as compared to sham and normal group. This showed that Partial Sciatic nerve ligation resulted in significant development of static mechanical hyperalgesia. Thus pain sensitivity is increased significantly due to static mechanical hyperalgesia. On day 28, of administration of Test composition significantly increased mechanical nociceptive threshold i.e. mean paw-withdrawal threshold at higher doses (i.e. 10 mg/kg, 30 mg/kg) as compared to PSNL control rats. This shows that treatment with instant composition showed significant reduction in pain sensitivity. Thus, the instant composition shows efficacy in reducing neuropathic pain or managing neuropathy.

TABLE 4

Effect of Test composition on Paw withdrawal threshold (g) in Von frey hair test in PSNL rats

| Days | Normal | Sham | PSNL Control | Test composition | | |
| --- | --- | --- | --- | --- | --- | --- |
| | | | | PSNL + 3 mg/kg | PSNL + 10 mg/kg | PSNL + 30 mg/kg |
| Baseline 0 (Before Treatment) | 75.33 ± 4.93 | 77.98 ± 2.64 | 24.00 ± 4.32$^{\#\#\#}$ | 21.85 ± 1.75$^{ns}$ | 22.61 ± 2.94$^{ns}$ | 23.26 ± 0.96$^{ns}$ |
| 28 (After Treatment) | 81.16 ± 3.95 | 79.40 ± 1.65 | 24.70 ± 2.27$^{\#\#\#}$ | 35.82 ± 2.53 | 50.38 ± 2.89*** | 69.12 ± 2.50*** |

Data was analysed by Two-Way ANOVA followed by Bonferroni's post tests *p<0.05, p<0.01, *p<0.001 as compared with PSNL control group and #p<0.05, ##p<0.01, ####p<0.001 as compared with sham group on respective days. ns—Non significant Example 8

Cold Hyperalgesia
Effect of Test Composition on Reaction Time (s) in Cold Bath Test:

Before initiation of treatment baseline reading are taken on day 0 and the doses are administered for 28 days. As shown in table 5, on day 0, mean paw withdrawal latency in PSNL control rats is decreased significantly as compared to sham and normal group. Thus pain sensitivity is increased significantly due to cold hyperalgesia. On day 28 of administration of Test composition significantly attenuated partial sciatic nerve ligation induced increase in spinal cold sensitivity, assessed by paw withdrawal latency i.e. reaction time at higher doses (10 and 30 mg/kg p.o.) as compared to PSNL control rats. This shows that treatment with instant composition showed significant reduction in cold sensitivity. Thus instant composition shows efficacy in reducing neuropathic pain or managing neuropathy.

TABLE 5

Effect of Test composition on reaction time (s) in cold bath test in PSNL rats

| Days | Normal | Sham | PSNL Control | Test composition | | |
|---|---|---|---|---|---|---|
| | | | | PSNL + 3 mg/kg | PSNL + 10 mg/kg | PSNL + 30 mg/kg |
| Baseline 0 (Before Treatment) | 14.22 ± 0.50 | 13.51 ± 0.67 | 2.63 ± 0.34$^{\#\#\#}$ | 2.65 ± 0.43$^{ns}$ | 2.46 ± 0.22$^{ns}$ | 2.91 ± 0.30$^{ns}$ |
| 28 (After Treatment) | 14.42 ± 0.85 | 14.00 ± 0.83 | 4.02 ± 0.79$^{\#\#\#}$ | 6.53 ± 0.92$^{ns}$ | 8.89 ± 0.46*** | 12.05 ± 0.37*** |

Data was analysed by Two-Way ANOVA followed by Bonferroni's post tests *p<0.05, p<0.01, *p<0.001 as compared with PSNL control group and #p<0.05, ##p<0.01, ####p<0.001 as compared with sham group on respective days. ns—Non significant Example 9

Heat Hyperalgesia
Effect of Test Composition on Reaction Time (s) in Plantar Test:

Before initiation of treatment baseline reading is taken on day 0 and the doses are administered for 28 days. As shown in table 6, on day 0, mean paw withdrawal latency in PSNL control rats is decreased significantly as compared to sham and normal group. Thus pain sensitivity is increased significantly due to thermal hyperalgesia. On day 28 of administration of Test composition significantly attenuated paw withdrawal latency i.e. reaction time at higher doses (10 and 30 mg/kg p.o.) as compared to PSNL control rats. This shows that treatment with instant composition showed significant reduction in heat sensitivity. Thus instant composition shows efficacy in managing neuropathic pain or managing neuropathy.

TABLE 6

Effect of Test composition on reaction time (s) in plantar test in PSNL rats

| Days | Normal | Sham | PSNL Control | Test composition | | |
|---|---|---|---|---|---|---|
| | | | | PSNL + 3 mg/kg | PSNL + 10 mg/kg | PSNL + 30 mg/kg |
| Baseline 0 (Before Treatment) | 7.46 ± 0.43 | 6.73 ± 0.33 | 1.66 ± 0.22$^{\#\#\#}$ | 1.61 ± 0.28$^{ns}$ | 1.26 ± 0.13$^{ns}$ | 1.48 ± 0.21$^{ns}$ |
| 28 (After Treatment) | 7.55 ± 0.38 | 7.31 ± 0.56 | 2.68 ± 0.35$^{\#\#\#}$ | 3.91 ± 0.24$^{ns}$ | 4.70 ± 0.30*** | 6.48 ± 0.24*** |

Data was analysed by Two-Way ANOVA followed by Bonferroni's post tests *p<0.05, p<0.01, *p<0.001 as compared with PSNL control group and #p<0.05, ##p<0.01, ####p<0.001 as compared with sham group on respective days. ns—Non significant Example 10

Effect of Test Composition on Motor Nerve Conduction Velocity (m/s):

After 28 day duration of induction of neuropathy by partial sciatic nerve ligation, MNCV in sciatic nerves from PSNL control measured in vivo and it is significantly decreased. When compared with sham operated rats there is significant decrease in nerve conduction velocity in PSNL control rats. On day 28 of administration of Test composition at higher doses (10 and 30 mg/kg p.o.) the nerve conduction velocity is significantly increased when compared with PSNL control rats (Table 7). This shows that treatment with instant composition showed significant reduction in neuropathic pain. Thus instant composition shows efficacy in managing neuropathic pain or neuropathy.

Group V: Fenugreek Extract Treated Group (30 mg/kg)

The sciatic nerve of the rats is exposed and they received injury. They are treated with Fenugreek extract at a dose of 30 mg/kg, p.o.

Group VI: Pinitol Stand-Alone Treated Group (30 mg/kg)

The sciatic nerve of the rats is exposed and they received injury. They are treated with Pinitol as a stand-alone at high dose of 30 mg/kg, p.o as shown in TABLE 8 below:

TABLE 8

| Group No. | Treatment | Dose (units) | Route of Administration | No. of animals (n) |
|---|---|---|---|---|
| 1 | Normal | Vehicle | Oral | 6 |
| 2 | Sham | Vehicle | Oral | 6 |
| 3 | PSNL Control | Vehicle | Oral | 6 |
| 4 | PSNL + Test Composition | 30 mg/kg | Oral | 6 |
| 5 | PSNL + Fenugreek extract | 30 mg/kg | Oral | 6 |
| 6 | PSNL + Pinitol stand-alone | 30 mg/kg | Oral | 6 |

TABLE 7

Effect of Test composition on Motor Nerve Conduction Velocity (m/s) in PSNL rats

| Days | Normal | Sham | PSNL Control | Test composition | | |
|---|---|---|---|---|---|---|
| | | | | PSNL + 3 mg/kg | PSNL + 10 mg/kg | PSNL + 30 mg/kg |
| 28 (After Treatment) | 25.11 ± 2.08 | 24.01 ± 1.39 | 8.58 ± 0.88#### | 10.11 ± 0.74$^{ns}$ | 15.75 ± 0.88** | 21.01 ± 0.51*** |

Example 11

Comparison of Efficacy of Test Composition Vs. Alcoholic Extract of Fenugreek Vs. Pinitol Stand-Alone on Motor Nerve Conduction Velocity (m/s):

To compare efficacy of test Composition with Alcoholic Extract of Fenugreek (30 mg/kg p.o) and Pinitol stand-alone (30 mg/kg) in neuropathy, PSNL rat model is used.

Grouping is done to carry out the test in the following manner:

Group I: Normal Group

The rats did not receive either surgery or injury for sciatic nerve. They received only vehicle (Distilled water).

Group II: Sham Group

The sciatic nerve of the rats is exposed, but they did not receive injury. They received only vehicle (Distilled water).

Group III: PSNL Control Group

The sciatic nerve of the rats is exposed and they received injury by a process where a 4-0 silk suture are inserted into the nerve with ⅜ curve, with a reverse-cutting mini needle and is tightly ligated so that the dorsal ⅓-½ of the nerve thickness are trapped in the ligature. They received only vehicle (Distilled water).

Group IV: Test Composition Treated Group (30 mg/kg)

The sciatic nerve of the rats is exposed and they received injury. They are treated with Test composition at a dose of 30 mg/kg, p.o.

Male wistar rats weighing 200-220 g average are used for the study. 500 g of fenugreek seeds is extracted by using alcoholic extraction procedure. This extract is obtained in a dry form by using vacuum evaporation technique.

After 28 day duration of induction of neuropathy by partial sciatic nerve ligation (PSNL), motor nerve conduction velocity in sciatic nerves from PSNL control measured in-vivo and it is significantly decreased. When compared with sham operated rats there is significant decrease in nerve conduction velocity in PSNL control rats. On day 28, the treatment with fenugreek extract at high dose of 30 mg/kg p.o. did not show any increase in nerve conduction velocity when compared with PSNL control rats.

However on day 28, the treatment with Pinitol stand-alone at a same dose showcased marginal effect in nerve conduction velocity when compared with PSNL control rats. After administration of Test composition (30 mg/kg p.o.) on day 28 of treatment the nerve conduction velocity is significantly increased when compared with PSNL control rats and Pinitol stand-alone group as well as illustrated below in Table 9. Thus, the test composition which comprises Pinitol, Eleutheroside C and sugars shows highly significant effect in reducing Neuropathic pain and bringing the nerve conduction velocity closer to the normal desired level.

TABLE 9

Effect of chronic administration of Test composition and Pinitol (stand-alone) on Motor Nerve Conduction Velocity (m/s) in PSNL rats

| Days | Normal | Sham | PSNL Control | Fenugreek extract (30) | Test Composition (30) | Pinitol stand-alone(30) |
|---|---|---|---|---|---|---|
| 28 (After Treatment) | 25.11 ± 2.09 | 24.01 ± 1.34$^{ns}$ | 8.58 ± 0.89$^{\#\#\#}$ | 10.11 ± 0.10$^{ns1}$ | 22.8 ± 0.54*** | 13.97 ± 1.02* |

Figure 5:
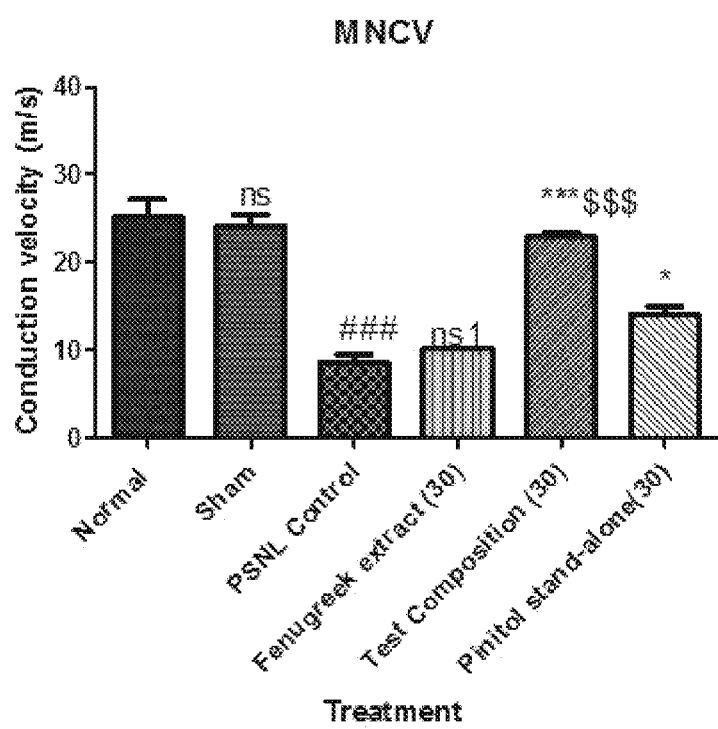
FIG. 5 illustrates the comparison of efficacy of test composition with Alcoholic Extract of Fenugreek and Pinitol stand-alone on Motor Nerve Conduction Velocity

The FIG. 5 illustrates the comparison of efficacy of test composition with Alcoholic Extract of Fenugreek and Pinitol stand-alone on Motor Nerve Conduction Velocity The data was analysed by one way ANOVA followed by Bonferroni's Multiple Comparison Test, wherein:
ns—non-significant Vs/normal;
$p<0.001$ v/s PSNL control;
*$p<0.05$, ***$p<0.001$ v/s PSNL control; and
$$$—$P<0.001$ v/s Pinitol stand-alone.

Example 12

Effect of Test Composition on Sciatic Nerve Crush Injury (SNCI) Induced Neuropathy in Rats The parameters taken into consideration:
1. Mechanical Hyperalgesia
   a. Randall-Selitto paw pressure test
   b. Von Frey hair test
2. Thermal Hyperalgesia
   a. Plantar test
3. Cold Hyperalgesia
   a. Cold bath test
4. Motor Nerve Conduction Velocity Grouping of Animals is Done in Following Manner:

Group I: Normal Group

The rats did not receive either surgery or injury for sciatic nerve. They received only vehicle (Distilled water).

Group II: Sham Group

The sciatic nerve of the rats is exposed, but they did not receive injury. They received only vehicle (Distilled water).

Group III: SNCI Control Group

The sciatic nerve of the rats is exposed and they received injury by a process where a 4-0 silk suture are inserted into the nerve with ⅜ curve, with a reverse-cutting mini needle and is tightly ligated so that the dorsal ⅓-½ of the nerve thickness are trapped in the ligature. They received only vehicle (Distilled water).

Group IV: Test Composition Treated Group (3 mg/kg)

The sciatic nerve of the rats is exposed and they received injury. They are treated with Test composition at a low dose of 3 mg/kg, p.o.

Group V: Test Composition Treated Group (10 mg/kg)

The sciatic nerve of the rats is exposed and they received injury. They are treated with Test composition at a medium dose of 10 mg/kg, p.o.

Group VI: Test Composition Treated Group (30 mg/kg)

The sciatic nerve of the rats is exposed and they received injury. They are treated with Test composition at a high dose of 30 mg/kg, p.o as shown in TABLE 8 below:

TABLE 10

Effect of Test Composition on Sciatic Nerve Crush Injury (SNCI) induced neuropathy in rats

| Group No. | Treatment | Dose (units) | Route of Administration | No. of animals (n) |
|---|---|---|---|---|
| 1 | Normal | Vehicle | Oral | 6 |
| 2 | Sham | Vehicle | Oral | 6 |
| 3 | SNCI Control | Vehicle | Oral | 6 |
| 4 | SNCI + Test Composition | 3 mg/kg | Oral | 6 |
| 5 | SNCI + Test Composition | 10 mg/kg | Oral | 6 |
| 6 | SNCI + Test Composition | 30 mg/kg | Oral | 6 |

Male wistar rats weighing 200-220 g average are used for the study. All the required parameters (pre-operative) are carried out in all rats before surgery. Under Ketamine anesthesia (80 mg/kg) and aseptic conditions the right sciatic nerve is exposed at thigh level and a sciatic nerve crush injury is created by a standard protocol. The animals are allowed to recover after surgery for 2 days. Before initiation of treatment baseline reading is taken on day 0 and the doses are administered as described in above table 8 for 28 days. Data analysis is performed using Graph Pad Prism 5.0 software (Graph Pad San Diego, Calif.). Statistical comparisons are made between drug treated groups and SNCI control animals. Data of disease activity index are statistically analyzed using two-way repeated ANOVA, Bonferroni's multiple range test is applied for post hoc analysis, while motor nerve conduction velocity is analyzed using one-way ANOVA, Dunnett's multiple range test is applied for post hoc analysis. A value of $p<0.05$ is considered to be statistically significant.

Example 13

Mechanical Hyperalgesia
A. Effect of Test Composition on Mean Applied Force (g) in Randall-Selitto Paw Pressure Test:

Before initiation of treatment baseline reading is taken on day 0 and the doses are administered for 28 days. As shown in below table 9, on day 0, mean applied force in SNCI control rats is decreased significantly as compared to sham and normal group. This showed that Sciatic nerve crush injury resulted in significant development of mechanical hyperalgesia, demonstrated by decrease in mean applied force on hind paw of SNCI control rats as compared to sham operated rats. Thus pain sensitivity is increased significantly due to mechanical hyperalgesia. On day 28 of administration of Test composition mechanical nociceptive threshold i.e. mean applied force increased significantly at higher doses (i.e. 10 mg/kg, 30 mg/kg) as compared to SNCI control rats. This shows that treatment with instant composition showed reduction in pain sensitivity. Thus instant composition shows efficacy in reducing neuropathic pain or managing neuropathy.

TABLE 11

Effect of Test composition on mean applied force (g) in Randall-Selitto paw pressure test sin SNCI rats

| Days | Normal | Sham | SNCI Control | Test composition | | |
|---|---|---|---|---|---|---|
| | | | | SNCI + 3 mg/kg | SNCI + 10 mg/kg | SNCI + 30 mg/kg |
| Baseline 0 (Before treatment) | 250.00 ± 18.44 | 242.50 ± 24.31 | 72.50 ± 14.18[####] | 62.50 ± 7.15[ns] | 62.50 ± 4.61[ns] | 75.00 ± 7.74[ns] |
| 28 (After treatment) | 245.00 ± 16.73 | 245.00 ± 25.88 | 67.50 ± 11.45[####] | 107.50 ± 12.50 | 170.00 ± 11.40*** | 202.50 ± 10.06*** |

Data was analysed by Two-Way ANOVA followed by Bonferroni's post tests *$p<0.05$, $p<0.01$, *$p<0.001$ as compared with PSNL control group and [#] $p<0.05$, [##] $p<0.01$, [####] $p<0.001$ as compared with sham group on respective days. ns—Non significant

[#####] $p<0.001$ as compared with sham group on respective days. ns—Non significant Example 14

Mechanical Hyperalgesia
B. Effect of Test Composition on Paw Withdrawal Threshold (g) in Von Frey Hair Test:

Before initiation of treatment baseline reading is taken on day 0 and the doses are administered for 28 days. However as shown in table 10, on day 0, mean paw-withdrawal threshold in SNCI control rats is decreased significantly as compared to sham and normal group. Thus pain sensitivity is increased significantly due to mechanical hyperalgesia. On day 28 of administration of Test composition mean paw-withdrawal threshold increased significantly at higher doses (i.e. 10 mg/kg, 30 mg/kg) as compared to SNCI control rats. This shows that treatment with instant composition showed reduction in pain sensitivity. Thus instant composition shows efficacy in reducing neuropathic pain or managing neuropathy.

Example 15

Cold Hyperalgesia
Effect of Test Composition on Reaction Time (s) in Cold Bath Test:

Before initiation of treatment baseline reading is taken on day 0 and the doses are administered for 28 days. As shown in table 11, on day 0, mean paw withdrawal latency in SNCI control rats is decreased significantly as compared to sham and normal group. Thus pain sensitivity is increased significantly due to cold hyperalgesia. On day 28 of administration of Test composition sciatic nerve crush injury induced increase in spinal cold sensitivity, assessed by paw withdrawal latency i.e. reaction time attenuated significantly at higher dose (30 mg/kg p.o.) as compared to SNCI control rats. This shows that treatment with instant composition

TABLE 12

Effect of Test composition on Paw withdrawal threshold (g) in Von frey hair test in SNCI rats

| Days | Normal | Sham | SNCI Control | Test composition | | |
|---|---|---|---|---|---|---|
| | | | | SNCI + 3 mg/kg | SNCI + 10 mg/kg | SNCI + 30 mg/kg |
| Baseline 0 (Before treatment) | 81.06 ± 6.65 | 80.98 ± 4.77 | 29.92 ± 3.63[####] | 26.23 ± 1.84[ns] | 29.45 ± 2.03[ns] | 29.90 ± 1.41[ns] |
| 28 (After treatment) | 83.56 ± 3.53 | 86.13 ± 4.55 | 30.16 ± 3.00[####] | 40.15 ± 3.48[ns] | 51.56 ± 3.33** | 68.13 ± 2.77*** |

Data was analysed by Two-Way ANOVA followed by Bonferroni's post tests *$p<0.05$, $p<0.01$, *$p<0.001$ as compared with PSNL control group and [#] $p<0.05$, [##] $p<0.01$, showed reduction in cold sensitivity. Thus instant composition shows efficacy in reducing neuropathic pain or managing neuropathy.

TABLE 13

Effect of Test composition on reaction time (s) in cold bath test in SNCI rats

| Days | Normal | Sham | SNCI Control | Test composition | | |
|---|---|---|---|---|---|---|
| | | | | SNCI + 3 mg/kg | SNCI + 10 mg/kg | SNCI + 30 mg/kg |
| 0 (Before Treatment) | 13.63 ± 1.08 | 12.70 ± 1.21 | 3.85 ± 0.91[###] | 3.55 ± 0.43[ns] | 3.88 ± 0.39[ns] | 3.97 ± 0.28[ns] |
| 28 (After Treatment) | 13.42 ± 0.77 | 12.96 ± 0.88 | 4.46 ± 0.37[###] | 5.81 ± 0.82[ns] | 7.75 ± 0.73[ns] | 11.13 ± 0.45*** |

Data was analysed by Two-Way ANOVA followed by Bonferroni's post tests *p<0.05, p<0.01, *p<0.001 as compared with PSNL control group and # p<0.05, ## p<0.01, #### p<0.001 as compared with sham group on respective days. ns—Non significant

Example 16

Heat Hyperalgesia

Effect of Test Composition on Reaction Time (s) in Plantar Test:

Before initiation of treatment baseline reading is taken on day 0 and the doses are administered for 28 days. As shown in table 12, on day 0, mean paw withdrawal latency in SNCI control rats is decreased significantly as compared to sham and normal group. Thus pain sensitivity is increased significantly due to thermal hyperalgesia. On 28th day, Administration of Test composition significantly attenuated paw withdrawal latency i.e. reaction time at higher dose (30 mg/kg p.o.) as compared to SNCI control rats. This shows that treatment with instant composition showed reduction in heat sensitivity. Thus instant composition shows efficacy in managing neuropathic pain.

Data was analysed by One-Way ANOVA followed by Dunnett's post tests *p<0.05, p<0.01, *p<0.001 as compared with SNCI control group and # p<0.05, ## p<0.01, #### p<0.001 as compared with sham group. ns—Non significant

Example 18

Effect of Test Composition in Patients Suffering from Neuropathic Pain

To study the efficacy of the test composition in managing Neuropathic pain, human anecdotal study is carried out. It is evaluated in 4 patients with an average age of over 50 years. The DN4 Questionnaire (Neuropathic Pain Diagnostic Questionnaire) is first used in patients to assess the type of pain whether it is a neuropathic or a nociceptive pain. Out of the 4 patients, treatment for only 3 patients is continued with Test composition. This is because, patient 4 showed symptoms of nociceptive pain.

TABLE 14

Effect of Test composition on reaction time (s) in plantar test in SNCI rats

| Days | Normal | Sham | SNCI Control | Test composition | | |
|---|---|---|---|---|---|---|
| | | | | SNCI + 3 mg/kg | SNCI + 10 mg/kg | SNCI + 30 mg/kg |
| Baseline 0 (Before Treatment) | 5.93 ± 0.59 | 5.93 ± 0.49 | 1.91 ± 0.30$^{\#\#\#}$ | 1.86 ± 0.13$^{ns}$ | 1.55 ± 0.41$^{ns}$ | 1.70 ± 0.13$^{ns}$ |
| 28 (After Treatment) | 6.00 ± 0.24 | 5.81 ± 0.29 | 2.10 ± 0.33$^{\#\#\#}$ | 3.10 ± 0.58$^{ns}$ | 3.91 ± 0.38$^{ns}$ | 4.90 ± 0.36*** |

Data was analysed by Two-Way ANOVA followed by Bonferroni's post tests *p<0.05, p<0.01, *p<0.001 as compared with PSNL control group and # p<0.05, ## p<0.01, #### p<0.001 as compared with sham group on respective days. ns—Non significant

Example 17

Effect of Test Composition on Motor Nerve Conduction Velocity (m/s):

After 28 day duration of induction of neuropathy by Sciatic nerve crush injury, MNCV in sciatic nerves from SNCI control measured in vivo and it is significantly decreased. When compared with sham operated rats there is significant decrease in nerve conduction velocity in SNCI control rats. After administration of Test composition (10 and 30 mg/kg p.o.) on day 28 of treatment the nerve conduction velocity is significantly increased when compared with SNCI control rats. Thus instant composition shows efficacy in managing neuropathic pain or neuropathy.

TABLE 16

DN4 Questionnaire

| Symptom/Sign Yes = 1:No = 0 | Patient Recorded Outcome | | | |
|---|---|---|---|---|
| | Patient 1 | Patient 2 | Patient 3 | Patient 4 |
| Does the pain have the following characteristic? | | | | |
| Burning | 1 | 0 | 1 | 0 |
| Painful cold | 0 | 1 | 1 | 1 |
| Tingling | 1 | 1 | 1 | 0 |
| Does the area of pain also have the following | | | | |
| Pins & needles | 1 | 1 | 1 | 1 |
| Numbness | 0 | 0 | 1 | 1 |
| Exam: Decrease in touch sensation (soft brush)? | 0 | 1 | 0 | 0 |
| Exam: Decrease in prick sensation (von Frey hair #13)? | 1 | 1 | 1 | 0 |

TABLE 15

Effect of Test composition on Motor Nerve Conduction Velocity (m/s) in SNCI rats

| Days | Normal | Sham | SNCI Control | Test composition | | |
|---|---|---|---|---|---|---|
| | | | | SNCI + 3 mg/kg | SNCI + 10 mg/kg | SNCI + 30 mg/kg |
| 28 (After Treatment) | 28.21 ± 2.37 | 22.90 ± 1.42 | 9.12 ± 0.90$^{\#\#\#}$ | 9.88 ± 0.74$^{ns}$ | 12.95 ± 1.558$^{ns}$ | 22.13 ± 1.30*** |

TABLE 16-continued

DN4 Questionnaire

| | Patient Recorded Outcome | | | |
|---|---|---|---|---|
| Symptom/Sign Yes = 1:No = 0 | Patient 1 | Patient 2 | Patient 3 | Patient 4 |
| Exam: Does movement of a soft brush in the area cause or increase pain? | 1 | 0 | 1 | 0 |
| Total | 5 | 6 | 7 | 3 |

Scale of type of pain: 0-3=likely nociceptive pain ≥4= likely neuropathic pain

Based on the above questionnaire, Patient 4 got rejected from study as the patient showed symptoms of nociceptive pain. Treatment for patients 1, 2 and 3 are continued with Test Composition.

The test composition for the 3 patients are given at a dose of 300 mg twice daily for a period of 2 months and the efficacy of the test composition is analysed on the basis of patient reported outcome taken at the beginning and end of the study period.

TABLE 17

| | Patient Recorded Outcome† | | | | | |
|---|---|---|---|---|---|---|
| | Patient 1 | | Patient 2 | | Patient 3 | |
| Symptoms | Before | After | Before | After | Before | After |
| Burning Sensation in area of pain | 4 | 3 | 2 | 1 | 4 | 3 |
| Pain triggered due to cold/heat water bath in area of pain | 3 | 2 | 3 | 0 | 4 | 2 |
| Tingling or Pricking Sensation in area of pain | 5 | 2 | 4 | 1 | 5 | 2 |
| Sensation of numbness in area of pain | 3 | 2 | 3 | 2 | 4 | 3 |
| Pain triggered due to light exposure | 3 | 1 | 4 | 3 | 3 | 2 |
| Sudden Pain attacks | 5 | 2 | 4 | 1 | 5 | 1 |
| Pain triggered by applying slight pressure with a finger in area of pain | 2 | 0 | 0 | 0 | 3 | 2 |

†Scale of Severity of Neuropathic Pain (0—Absence; 1—Hardly Noticed; 2—Mild; 3—Moderate; 4—Strong; 5—Very Strong)

Following the initiation of administration of the test composition, the subjects reported reduction in the frequency of sudden pain attacks, decrease in the intensity of burning sensation, tingling, numbness and pain caused by triggers such as touch, hot/cold water bath, light exposure etc.

The test composition is found to be useful in managing Neuropathic pain in human subjects.

We claim:

1. A process of obtaining a composition consisting essentially of eleutheroside-C, pinitol, raffinose, stachyose and sucrose, optionally along with pharmaceutically acceptable excipient, said method comprising acts of:
   a. contacting sample of *Trigonella* species with a solvent in a chromatographic column, followed by draining the solvent to obtain de-lipidized solution;
   b. extracting the de-lipidized solution with hydro-alcohol mixture to obtain a first extract;
   c. exposing the first extract to acid cation exchange resin column, followed by passing the extract through a macro reticular polymeric adsorbent column to obtain a second extract;
   d. heating the second extract and re-exposing the same to acid cation exchange resin column followed by optionally filtering and neutralizing the extract;
   e. concentrating the extract of step (d); and
   f. optionally mixing the concentrated extract of step (e) with pharmaceutically acceptable excipient to obtain the composition.

2. The process as claimed in claim 1, wherein the sample of step (a) is a seed of *Trigonella* species; and wherein the seed is flaked.

3. The process as claimed in claim 1, wherein the solvent is N-butyl alcohol; and wherein the solvent exposure is for a time period ranging from about 4 hr to about 8 hr.

4. The process as claimed in claim 1, wherein the hydro alcohol mixture comprises water:ethyl alcohol at a ratio ranging from about 1:0.5 to about 1:3; and wherein the extraction is carried out for a time period ranging from about 6 hr to about 10 hr and at a temperature ranging from about 40° C. to about 80° C.

5. The process as claimed in claim 1, wherein exposure of the first extract to the ion exchange column is for a time period ranging from about 4 hr to about 6 hr.

6. The process as claimed in claim 1, wherein the heating is carried out at a temperature ranging from about 50° C. to about 70° C.; and wherein the neutralization is carried out by exposure to neutralizing macro porous type 1 resin.

7. The process as claimed in claim 1, wherein the concentration is under vacuum carried out at a temperature ranging from about 40° C. to about 50° C.

8. The process of claim 2, wherein the *Trigonella* species is *Trigonella foenum greacum*.

9. The process of claim 4, wherein the temperature range is from about 62° C. to about 65° C.

10. The process of claim 6, wherein the heating is carried out at a temperature ranging from about 60° C. to about 65° C.

* * * * *